(12) United States Patent
Theoharides

(10) Patent No.: US 7,799,766 B2
(45) Date of Patent: *Sep. 21, 2010

(54) COMPOSITION FOR TREATING HORMONALLY-DEPENDENT CANCERS

(75) Inventor: Theoharis C. Theoharides, Brookline, MA (US)

(73) Assignee: Theta BioMedical Consulting & Development Co., Inc., Brookline, MA (US)

( * ) Notice: Subject to any disclaimer, the term of this patent is extended or adjusted under 35 U.S.C. 154(b) by 1024 days.

This patent is subject to a terminal disclaimer.

(21) Appl. No.: 10/811,838

(22) Filed: Mar. 30, 2004

(65) Prior Publication Data

US 2004/0180106 A1   Sep. 16, 2004

(51) Int. Cl.
A01N 43/04 (2006.01)
A61K 31/35 (2006.01)
A61K 31/56 (2006.01)
A61K 36/00 (2006.01)

(52) U.S. Cl. .......................... 514/55; 514/456; 514/178; 424/776

(58) Field of Classification Search .................. 514/55, 514/456, 178
See application file for complete search history.

(56) References Cited

U.S. PATENT DOCUMENTS

| | | | |
|---|---|---|---|
| 4,265,823 A * | 5/1981 | Nobile | .................. 552/504 |
| 5,223,257 A | 6/1993 | Arora | |
| 5,250,529 A | 10/1993 | Theoharides | |
| 5,260,335 A | 11/1993 | Wagner et al. | |
| 5,648,355 A | 7/1997 | Theoharides | |
| 5,795,905 A | 8/1998 | McCarthy et al. | |
| 5,804,594 A | 9/1998 | Murad | |
| 5,855,884 A | 1/1999 | Theoharides | |
| 5,858,371 A * | 1/1999 | Singh et al. | ........... 424/731 |
| 5,876,744 A | 3/1999 | Della Valle et al. | |
| 5,972,999 A | 10/1999 | Murad | |
| 5,980,865 A | 11/1999 | Ahmed | |
| 5,994,357 A | 11/1999 | Theoharides | |
| 6,020,305 A | 2/2000 | Theoharides | |
| 6,136,795 A | 10/2000 | Florio | |
| 6,162,787 A | 12/2000 | Sorgente et al. | |
| 6,211,195 B1 | 4/2001 | Webb et al. | |
| 6,492,429 B1 | 12/2002 | Graus et al. | |
| 6,586,448 B1 | 7/2003 | DeNinno et al. | |
| 6,624,148 B2 * | 9/2003 | Theoharides | .................. 514/27 |
| 6,635,625 B2 * | 10/2003 | Theoharides | .................. 514/54 |
| 6,641,806 B2 * | 11/2003 | Theoharides | ............. 424/78.05 |
| 6,645,482 B2 * | 11/2003 | Theoharides | ............. 424/78.05 |
| 6,689,748 B1 | 2/2004 | Theoharides | |
| 6,765,008 B1 | 7/2004 | Chen | |
| 6,984,667 B2 * | 1/2006 | Theoharides | .................. 514/27 |
| 7,115,278 B2 * | 10/2006 | Theoharides | ................ 424/451 |
| 2001/0000340 A1 | 4/2001 | Chen et al. | |
| 2001/0009680 A1 | 7/2001 | Rang et al. | |
| 2002/0028779 A1 * | 3/2002 | High et al. | .................... 514/27 |
| 2002/0146393 A1 | 10/2002 | Bell et al. | |
| 2002/0150605 A1 | 10/2002 | Yui et al. | |
| 2004/0024016 A1 | 2/2004 | Sugamata | |
| 2005/0220909 A1 | 10/2005 | Theoharides | |
| 2006/0128655 A1 | 6/2006 | Falk et al. | |
| 2006/0210551 A1 | 9/2006 | Lindsberg et al. | |
| 2007/0141187 A1 | 6/2007 | Theoharides | |

FOREIGN PATENT DOCUMENTS

| | | |
|---|---|---|
| EP | 0426479 | 5/1991 |
| GB | 2105193 | 9/1984 |
| IT | 1290440 | 9/1998 |
| JP | 06-016531 A * | 1/1994 |
| WO | WO 97/21434 | 6/1997 |
| WO | WO-9721434 | 6/1997 |
| WO | WO-98/33494 | 8/1998 |
| WO | WO 9921434 A1 * | 5/1999 |
| WO | WO-00/78320 | 12/2000 |

OTHER PUBLICATIONS

Ip et al. Functionality of estrogen receptr and tamoxifen treatment of R3327 Dunning Rat prostate Adenocarcinoma, Cancer Research, 1980, vol. 40, p. 2188-2193.*
Widyarini et al. Isoflavonoid compounds from Red Clover (*Trifolium pratense*) protect from inflammation and immune Suppression induced by UV Radiation, Photochemistry and photobiology, 2001, vol. 74, No. 3, p. 465-470.*
Dr. Duke, Phytochemical and Ethnobotanical Database, Chemical in: *Olea europaea* subsp. *europaea* (Oleaceae)—Olive; URL, <HTTP://WWW.ARS-GRIN.GOV/CGI-BIN/DUKE/FARMACY2.PL> pp. 1-5.*
JP06-016531 English translation (machine).*
Dr. Duke; Phytochemical and Ethnobotanical Databases; Chemicals in: *Olea europaea* Subspo *europaea* (Oleaceae)—Olive; URL / www.ars-grin.gov/cgi-bin/duke/farmacy2.pl>, pp. 1-5; 2006.
International Search Report and Written Opinion, International Patent Application No. PCT/US08/86059, mailed Jan. 26, 2009 (7 pages).

(Continued)

*Primary Examiner*—Shengjun Wang
(74) *Attorney, Agent, or Firm*—Wilmer Cutler Pickering Hale & Dorr LLP.

(57) ABSTRACT

Compositions with synergistic anti-inflammatory effects in inflammatory diseases resulting from activation and consequent degranulation of mast cells and followed by secretion of inflammatory biomolecules from the activated mast cells, composed of a heavily sulfated, non-bovine proteoglycan such as shark cartilage chondroitin sulfate C, an unrefined olive kernel oil/extract that increases absorption of these compositions in various routes of administration, and one or more of a hexosamine sulfate such as D-glucosamine sulfate, a flavone such as quercetin, S-adenosylmethionine, a histamine-1 receptor antagonist, a histamine-3 receptor agonist, an antagonist of the actions of CRH, caffeine, and a polyamine.

21 Claims, No Drawings

OTHER PUBLICATIONS

Russell, A.L. and McCarty, M.F. "Glucosamine for migraine prophylaxis?" Medical Hypotheses, 55(3): 195-198 (2000).

Matsuda, K. et al., "Inhibitory Effects of Sialic-Acid- or N-Acetylglucosamine-Specific Lectins on Histamine Release Induced by Compound 48/80, Bradykinin and a Polyethylenimine in Rat Peritoneal Mast Cells," Jpn. J. Pharmacol., 64: 1-8 (1994).

Trichopoulou, A. et al., "Cancer and Meditarranean Dietary Traditions," Cancer Epidemiology, Biomarkers, & Prevention, vol. 9: 869-873 (Sep. 2000).

Theoharides, T.C., "The Mast Cell: A Neuroimmunoendocrine Master Player," Int. J. Tiss. Reac. XVIII(1), 1-21 (1996).

Theoharides, T.C., "Histamine2 (H2)-Receptor Antagonists in the Treatment of Urticaria," Drugs 37: 345-355 (1989).

Theoharides, T. "Mast Cells and Migraines," Brief Proposal, pp. 627-675 (1983).

Morrow, J. et al., "Indentification of Skin as a Major Site of Prostaglandin D2 Release Following Oral Administration of Niacin in Human," J. Invest. Derm., vol. 98(5): 812-815 (1992).

Weston, A. et al., "Terminal Ileal Mucosal Mast Cells in Irritable Bowel Syndrome," Dig. Diseases and Sci., vol. 38(9): 1590-1595 (Sep. 1993).

Shapiro, G. et al., "Cromolyn Sodium: A Review," Pharmacotherapy, vol. 5(3): 156-170 (May/Jun. 1985).

Database WPI: 2001-358435—XP002221703, "Compositions comprising hyaluronic acid and flavonoids," (2 pages).

International Search Report issued for PCT/US02/00476, dated Dec. 16, 2002 (6 pages).

Parodi et al., Arch. Psicol. Neurol. Psichiatr. vol. 49(3): 299-303 (1988).

Split et al., Headache, vol. 24(30): 147-149 (1984).

Unlisted Drugs, vol. 20(11): 167 (Nov. 1968).

Koblenzer, C.S. "Neurotic excoriations and dermatitis artefacta," Dermatologic Clinics, vol. 14(3): 447-455 (Jul. 1996).

Tauberg, J. et al., "Stress-induced urticaria associated with local anesthetic administration," Anesthesia Progress, vol. 30(6): 199-200 (1983).

Theoharides, T.C. "Mast Cells: The Immune Gate to the Brain," Life Sciences, vol. 46: 607-617 (1990).

Lambracht-Hall, M. et al., "Serotonin Release From Rat Brain Mast Cells," Neuroscience, vol. 39(1) 199-207 (1990).

Dimitriadou, V. et al., Histochemical and Ultrastructural Characteristics of Rat Brain Perivascular Mast Cells Stimulated With Compound 48/80 and Carbachol, Neuroscience, vol. 39(1): 209-224 (1990).

Pearce, F.L. "Mast cell heterogeneity," TIPS: 165-167 (Apr. 1983).

Theoharides, T.C. and Douglas, W.W. "Somatostatin Induces Histamine Secretion From Rat Peritoneal Mast Cells," Endocrinology, vol. 102(5): 1637-1640 (Nov. 7, 1977).

Sundaram, K. et al., "Antagonists of luteinizing hormone releasing hormone bind to rat mast cells and induce histamine release," Agents and Actions, vol. 25(3/4): 307-313 (1988).

Prior, A. and Read, N.W. "Reduction of rectal sensitivity and postprandial motility by granisetron, a 5HT3 receptor antagonist, in patients with irritable bowel syndrome (IBS)," Brit. Soc. of Gasteroent., A1174 (1 page).

Mathias, J. et al., "Debilitating 'Functional' Bowel Disease Controlled by Leuprolide Acetate, Gonadotropin-Releasing Hormone (GnRH) Analog," Digestive Diseases and Sciences, vol. 34(5): 761-766 (May 1989).

Read, N.W. "Irritable bowel syndrome (IBS)—definition and pathophysiology,", vol. 130: 7-13 (1987).

Stefanini, G.F. et al., "Oral disodium cromoglycate treatment on irritable bowel syndrome: an open study on 101 subjects with diarrheic type," vol. 87: 55-57 (1992).

International Search Report issued for PCT/US95/01392, dated May 31, 1995 (4 pages).

Hendriks, J. et al., "Flavonoids Influence Monocytic CTPase Activity and Are Protective in Experimental Allergic Encephalitis," J. Exp. Med., vol. 200(12): 1667-1672 (2004).

Mezzapesa, D. et al., "Glatiramer acetate in multiple sclerosis," Expert Rev. Neurotherapeutics (5)4: 451-458 (2005).

Gupta, E. et al., "Lovastatin and Extended-Release Niacin Combination Product: the First Drug Combination for the Management of Hyperlipidia," Heart Disease, vol. 4, 124-137 (2002).

Owens, M.J. and Nemeroff, C.B., "Physiology and Pharmacology of Corticotropin-releasing Factor," Pharmacological Reviews, vol. 43(4): 425-615 (1991).

Devlin, Thomas (ed): Textbook of Biochemistry with Clinical Correlations, 2nd Edition: Ch. 8.5-8.6, 345-351 (1982).

Simopoulos, A.P., Visioli F. (eds): Mediterranean Diets. World Rev. Nutr. Diet. Basel, Karger, vol. 87: 56-77 (2000).

Urade, Y. et al., "The Major Source of Endogenous Prostaglandin D2 Production is Likely Antigen-Presenting Cells," J. Immunol., 143(9): 2982-2989 (Nov. 1, 1989).

Lidor, C. et al., "Osteoporosis as the Sole Presentation of Bone Marrow Mastocytosis," J. Bone Min Res., vol. 5(8): 871-876 (1990).

Shoskes, D., et al., "Quercetin in men with category III chronic prostatis: a preliminary prospective, double-blind, placebo-controlled trial," Urology, 54(6): 960-963 (1999).

Seibold, J. et al., "Dermal Mast Cell Degranulation in Systemic Sclerosis," Arth. and Rheuma., vol. 33(11): 1702-1709 (Nov. 1990).

Rockoff, S.D. and Armstrong, J.D. "Parathyroid Hormone as a Stimulus to Mast Cell Accumulation in Bone," Calc. Tiss. Res., 5: 49-55 (1970).

Morrow, J.D., et al., "Release of markedly increased quantities of prostaglandin D2 in vivo in humans following the administration of nicotinic acid," Prostaglandins, vol. 38(2): 263-274 (1989).

Boushey, R. et al., "Adrenal Cortical Carcinoma," Curr. Treatment Op. Oncol., 2: 355-364 (2001).

Chines, A. et al., "Systemic Mastocytosis Presenting as Osteoporosis: A Clinical and Histomorphometric Study," J. Clin. Endocrinol. and Metab., vol. 72(1): 140-144 (1991).

Singleton, V.L. and Rossi, Jr., Joseph, "Colorimetry and Total Phenolics With Phosphomolybdic-Phosphotungstic Acid Reagents," Phenolics Determination, pp. 144-158.

* cited by examiner

COMPOSITION FOR TREATING HORMONALLY-DEPENDENT CANCERS

BACKGROUND OF THE INVENTION

The invention is generally related to the treatment of inflammatory conditions. More specifically, the invention is related to compositions containing inhibitors of mast cell activation and secretion such as a proteoglycan that are designed to be used as dietary supplements or adjuvants to conventional approved medications for the relief of inflammatory conditions.

There have been a number of mostly anecdotal reports that the proteoglycan chondroitin sulfate, as well as glucosamine sulfate, a product of the intestinal breakdown of proteoglycans, may be helpful in relieving the pain of osteoarthritis: Shute N. Aching for an arthritis cure. *US News and World Report*, Feb. 10, 1997. Cowley G. The arthritis cure? *Newsweek*, Feb. 17, 1997; Foreman J., People, and their pets, tout arthritis remedy. *The Boston Globe*, Apr. 7, 1997; Tye L. Treatment gains scientific attention. *The Boston Globe*, Sep. 25, 2000.

A recent meta-analysis showed potential therapeutic benefit of chondroitin sulfate and/or glucosamine in osteoarthritis [McAlindon et al. *J Am Med Assn.* 283:1469 (2000)], while a double-blind clinical trial with glucosamine showed definite benefits in osteoarthritis with respect to both pain and radiographic joint appearance [Reginster et al., *Lancet* 337: 252 (2001)]. However, less than 5% of the chondroitin sulfate in commercially available preparations is absorbed orally, because the size of the molecule and the degree of sulfation impede its absorption from the gastrointestinal tract. Furthermore, such commercial preparations use chondroitin sulfate obtained from cow trachea, with the possible danger of contracting spongiform encephalopathy or "mad cow disease". In fact, the European Union has banned even cosmetics that contain bovine-derived products.

Theoharides et al., *British Journal of Pharmacology* 131: 1039 (2000) indicated for the first time how proteoglycans such as chondroitin sulfate may work. The paper reported that chondroitin sulfate and, to a lesser degree, glucosamine sulfate, inhibit activation of mast cells that are known to trigger allergy and asthma. This discovery is the basis for Theoharides, U.S. patent application Ser. Nos. 09/056,707, filed Apr. 8, 1998 and 09/773,576, filed Feb. 2, 2001.

Mast cells are also now recognized as important causative intermediary in many painful inflammatory conditions[Galli, *N Eng J Med.* 328:257 (1993); Theoharides, *Int J Tissue Reactions* 18:1 (1996)], such as insterstitial cystitis and irritable bowel syndrome [Theoharides, *Ann NY Acad, Sci.* 840: 619 (1998)], as well as in migraines and possibly multiple sclerosis [Theoharides, *Persp Biol Med.* 26:672 (1983); Theoharides, *Life Sci* 46:607 (1996)]. In fact, glucosamine was recently considered to be prophylactic for migraines [Russell, *Med Hypoth* 55:195 (2000)].

Mast cells are increasingly implicated in conditions involving inflamed joints, such as in osteoarthritis and rheumatoid arthritis, through activation of local mast cells by, for example, neuropeptides, such as Substance P. Additional indirect evidence also supports the involvement of mast cells in bone resorption: (a) systemic mastocytosis is invariably associated with osteoporosis; (b) inhibition of mast cell mediator release reversed lytic bone changes; (c) depletion of mast cells inhibited bone resorption in organ culture; (d) human synovial mast cells were shown to secrete in response to allergic and non-immunologic stimuli; (e) human mast cells release the cytokine IL-6 and (f) IL-6 has been definitively linked to bone resorption and osteoporosis.

It was recently shown that chondroitin sulfate's ability to inhibit the activation of mast cells compliments the inhibitory effects on mast cell activation of another class of naturally occurring compounds, the flavonoids [Middleton et al. *Pharm Rev* 52:1 (2000)]. Certain plant flavones (in citrus fruit pulp, seeds, sea weed) are now recognized as anti-allergic, anti-inflammatory, anti-oxidant and cytoprotective with possible anti-cancer properties. Only some flavonoids that belong to the subclass of flavones, e.g., quercetin, inhibit mast cell activation.

Quercetin inhibits secretion from human activated mast cells [Kimata et al. *Allergy* 30:501(2000)], and has also been used effectively for the treatment of chronic prostatitis [Shoskes et al., *Urology* 54:960 (1999)]. However, other flavonoids may have opposite effects. Use of the term "bioflavonoids" or "citrus flavonoids" in certain commercial products, therefore, provides little information, and may include molecules that have detrimental effects; for example, soy contains isoflavones that have estrogen-like activity that worsens inflammatory conditions.

Copending U.S. patent application Ser. Nos. 09/056,707, filed Apr. 8, 1998, and divisional 09/773,576 claim the oral use of proteoglycans, without and with flavonoids, for the treatment of mast cell activation-induced diseases. Absorption of these compositions from the gastrointestinal tract and synergism with other treatment modalities were not addressed in these applications.

Applicant has described the use of antagonists of the action of Corticotropin Releasing Hormone (also known as Corticotropin Releasing Factor) in inhibiting myocardial mast cell activation in myocardial ischemia (copending U.S. patent application Ser. No. 08/858,136, filed May 18, 1997), in treating stress-induced skin disease (U.S. Pat. No. 6,020,305) and stress-induced migraine headaches (U.S. Pat. No. 5,855, 884), the contents of which are incorporated herein by reference. The synergistic effects of the compositions of the present invention that include antagonists of the actions of Corticotropin Releasing Hormone ("CRH") on mast cells were not recognized at the time of the previous studies. The word "antagonists" in connection with CRH is intended herein to include any molecule that prevents the actions of CRH on target cells, and includes, but is not limited to, anti-CRH neutralizing antibodies or binding proteins, or molecules preventing the release of CRH at local sites (see below for details).

Applicant has also described a method for treating patients with mast cell derived molecules-induced interstitial cystitis with histamine-1 receptor antagonists (U.S. Pat. No. 5,994, 357). Treatment of mast cell molecules-induced migraines with histamine-1 receptor antagonists is the subject of Theoharides U.S. Pat. No. 5,855,884. Histamine-3 receptor agonists as pharmaceutical agents in mast cell-involved diseases are described in Theoharides U.S. Pat. No. 5,831,259. The contents of these three patents are incorporated herein by reference. At the time of this invention the synergistic effects of the present compositions with such antagonists had not yet been recognized.

An important need therefore exists for compositions for administration to human patients being treated for mast cell-induced inflammatory diseases by various modalities, that are synergistic in that they have stronger effects than the sum of the effects of the individual components, and also synergistic with conventional clinical treatments of inflammatory conditions. "Synergistic" is also intended to mean: "coordinated or correlated action by two or more structures or drugs" [Stedman's Medical Dictionary, 23rd edition, Williams & Wilkins, Baltimore, 1976]. An important need also exists for formulations that increase the absorption from the gastrointestinal tract, nasal passages and skin surface of the compositions of the invention. Such formulations have been discovered, and are described below.

SUMMARY OF THE INVENTION

The invention comprises compositions for human use containing a heavily sulfated proteoglycan, with or without an unrefined olive kernel extract, and one or more active ingredients selected from the group consisting of a sulfated hexosamine, a flavonoid compound, S-adenosylmethionine ("SAM"), histamine-1 receptor antagonists, histamine-3 receptor agonists, antagonists of the actions of CRH, caffeine, folic acid, rutin, polyunsaturated fatty acids, and polyamines, together with appropriate excipients and carriers, said compositions having improved absorption from the gastrointestinal tract, skin surface, and nasal and pulmonary surfaces, and anti-inflammatory effects synergistic with each other and synergistic with available conventional clinical treatment modalities.

In one embodiment, the sulfated glucosamine is D-glucosamine sulfate, the proteoglycan is non-bovine chondroitin sulfate, and the flavone is quercetin.

In an other embodiment, compositions may also contain antagonists of the effects of CRH on mast cells or other target cells of the myocardium, gastric mucosa, urinary bladder, skin, meningeal membranes, and blood-brain barrier.

In still another embodiment, the inventive compositions are used against superficial vasodilator flush syndromes.

In still another embodiment, the inventive compositions may be used as coatings on medical devices, not only to protect surrounding tissues from inflammation due to the devices, but also to treat innate inflammation in surrounding tissues.

In another embodiment, the inventive compositions are used against the inflammatory processes of endometriosis.

In yet another embodiment, the inventive compositions are used against the inflammatory components of hormonally-related cancers, such as breast, testicular, ovarian and uterine cancers, and when supplemented with chemotherapeutic agents are used against the cancer itself.

In still another embodiment, the inventive compositions may be used in the treatment of multiple sclerosis.

In another embodiment, the inventive olive kernel extract is used to improve the absorption of drugs across membrane barriers in the body, such as those of the intestine, skin and pulmonary alveoli.

In yet another embodiment, the inventive compositions may be used in the treatment of fibromyalgia.

The inventive olive kernel extract may be used to increase the absorption of difficultly-absorbable drugs across the intestine, skin and pulmonary alveoli.

DETAILED DESCRIPTION OF THE PREFERRED EMBODIMENTS OF THE INVENTION

It has been discovered that a combination of a sulfated proteoglycan, with or without a unique unrefined olive kernel extract, with one or more of a sulfated D-hexoseamine, a flavone or isoflavone, CRH antagonists, histamine-1 receptor antagonists, histamine-3 receptor agonists, polyamines, rutin and caffeine has synergistic anti-inflammatory effects when used as a dietary supplement, a topical product or an aerosol for nasal or pulmonary administration, without or with a conventional clinical treatment for inflammatory diseases. Within the present context, such inflammatory diseases result from the activation, degranulation and consequent secretion of inflammatory biochemicals from mast cells, and the resultant inflammatory diseases include the group consisting of: allergic inflammation, arthritis (to include osteoarthritis and rheumatoid arthritis), fibromyalgia, inflammatory bowel disease, interstitial cystitis, irritable bowel syndrome, migraines, atherosclerosis, coronary inflammation, ischemia, chronic prostatitis, eczema, multiple sclerosis, psoriasis, sun burn, periodontal disease of the gums, superficial vasodilator flush syndromes, hormonally-dependent cancers, endometriosis and medical devices. The olive kernel extract alone may be used to improve the transmembrane transport of difficultly-absorbable drugs in the intestine, skin and pulmonary alveoli.

In a highly preferred embodiment, the sulfated proteoglycan is non-bovine chondroitin sulfate, preferably from shark cartilage, which blocks mast cell activation, degranulation and consequent secretion of inflammatory biochemicals from the mast cells. Other natural sulfated proteoglycans suitable for practicing this invention include keratan sulfate, dermatan sulfate and hyaluronic acid sodium salt (sodium hyaluronate). The preferred biological source of the chondroitin sulfate is shark cartilage which is more-highly sulfated than the common commercial chondroitin sulfate isolated from cow trachea; the shark cartilage source also avoids the potential dangers associated with bovine sources.

The highly preferred flavone is quercetin which inhibits secretion of inflammatory molecules from mast cells by affecting moesin, a unique 78 kDa mast cell protein [Theoharides et al. *J Pharm Exp Therap* 294:810 (2000)]. In addition to quercetin, other flavones suitable in carrying out the invention include the quercetin glycoside rutin, myricetin, genistein, kaempferol, the isoflavone phenoxodiol, and the kaempferol glycoside astrazaline.

The olive kernel extract product component of the inventive compositions is preferably an unrefined (first pressing, filtered, oleic acid-related acidity <3%, water content <1%) extract product produced, for one source, on the island of Crete in Greece. This kernel extract product is especially prepared by applicant's process consisting essentially of: (1) harvesting first collection ripe olives, preferably in December; (2) compressing the oil from the flesh of the ripe olives; (3) washing the kernels remaining after step (2) with water to remove debris; (4) drying the washed kernels with a stream of hot air; (5) crushing the dried kernels to produce an extract; (6) extracting the extract from step (5) with an organic solvent (e.g., hexane, heptane, octane) plus steam; (7) removing particulate matter from the organic extract by centrifugation or microfiltering through 1-2 micron pore size filters; (8) evaporating the organic solvent and water from the clarified extract of step (7) by maintaining the extract at 86-100 degrees C while percolating helium (to avoid oxidation) through the fluid, which process reduces the water content to <1%, the acidity (as oleic acid) to <3%; and, the organic solvent to <1%; and (8) storing the final kernel extract product in the absence of air.

The inventive olive kernel extract surprisingly has the unique property of increasing absorption of the other components of the anti-inflammatory compositions through the intestinal mucosa or skin, and also adds its own content of important anti-oxidants, such as omega fatty acids (e.g., eicosapentanoic acid) and alpha tocopherol. The polyphenols found in such olive kernel extracts also have anti-inflammatory effects in, for example, arthritis [Martinez-Dominguez et al., *Inflamm. Res*. 50:102 (2001)]. E.B.E.K., Inc., Commercial, Industrial Enterprises of Crete, 118 Ethnikis Antistasecos, Heraklion, Crete, 71306, Greece, will prepare the extract product according to applicant's above-described procedure for commercial users.

In addition to its usefulness in increasing the absorption of the inventive macromolecular compositions across the intestinal wall and the skin, the inventive olive kernel extract product is useful in aiding the dissolution of other drugs prior to administration to a patient, and is useful in promoting the absorption of other difficultly-absorbable drugs, e.g., the HDL-increasing drug torcetrapib (DeNinno et al. U.S. Pat. No. 6,586,448), across intestinal mucosa, oral mucosl, nasal mucosa, and skin of patients.

Supplementation of the compositions described above with the methylation reagent S-adenosylmethionine ("SAM") adds antioxidant, anti-inflammatory and cytoprotective properties, particularly in inflammatory joint diseases. Addition of SAM also accelerates metabolism of homocysteine, which amino acid has been implicated in coronary disease, to cysteine, which is harmless. Folic acid may be added to certain of the present formulations for similar reasons.

Another supplement to the basic compositions of the invention is a histamine-1 receptor antagonist, such as hydroxyzine, merelastine, azelastine, azatadine and cyproheptadine. Other histamine-1 receptor antagonists are described in Table 25-1 in Goodman and Gilman's The Pharmaceutical Basis of Therapeutics, 9$^{th}$ ed., New York, 1996. Histamine-3 receptor agonists are described in the Theoharides patents listed above.

Inhibitors of mast cell activation and secretion of inflammatory biochemicals may be used in the treatment of inflammatory processes such as superficial vasodilator syndrome, such as occurs in menopausal-associated flush, carcinoid flush, MSG-associated flush, and niacin-associated flush.

Hormone-dependent cancers, including the estrogen/progestin linked ovarian, uterine, breast, and endometrial cancers, and the androgen-linked testicular cancers, are associated with tissue inflammation. These inflammations can be treated with chondroitin sulfate, quercetin, genestein, phenoxodiol isoflavone, olive kernel oil/extract, and, optionally, chemotherapeutic agents such as tomoxifen or raloxifen.

Pelvic inflammatory conditions, such as presents in endometriosis, can also be treated with the inventive compositions. Particularly useful in this regard are compositions delivering 50-300 mg/day of chondroitin sulfate, quercetin or myricetin, and hydroxyzine.

The inventive compositions may also be used as coatings on implanted medical devices, which devices may lead to or be associated with inflammation of surrounding tissues, in order to provide protection against such inflammations. Not only can the coating of such medical devices inhibit or protect against inflammation caused by the device itself, but the coated devices can also be used to deliver the inventive compositions to innately inflamed tissues due to other causes. Such medical devices include artificial skins (scaffolding such as naturally occurring polymers, e.g., collagen; man-made polymers, e.g., PTFE, Dacron, PET or polyethylene; self-degrading man-made polymers, e.g., PLA or PGA; biopolymer matrices from animal tissues including fetal and neonatal tissues to be used as tissue engineering scaffolds (cf. Bell et al., U.S. patent application Pub. No. 20020146393)), artificial joints, band-aids, stents for blood vessels, artificial blood vessels, pacemakers, stents for abdominal support in hernia repair, tissue transplants, prostheses, breast implants, etc. Particularly useful in this regard are compositions containing heavily sulfated, non-bovine proteoglycans (e.g., chondroitin sulfate) and flavonoids (e.g., quercetin, myricetin, gentistein).

Sources of CRH antagonists include, in addition to the Theoharides patents listed in the Background section above: Neurocrine Biochem. Inc.'s D-Phe 12 Nle Ala32,21,38hCRH (12-41)NH2, cat no. 1P-36-41; Pfizer non-peptide CP-154, 526-1; Sigma Chem., St. Louis anti-CRH polyclonal antiserum; and Pfizer, N.Y. patents and applications: U.S. Pat. No. 6,211,195, U.S. Pat. No. 5,795,905, PCT/IB95/00573, PCT/IB95/00439, U.S. Pat. Ser. No. 08/448,539, U.S. Pat. Ser. No. 08/481,413, U.S. Pat. Ser. No. 09/735,841, and in Owens et al. Pharm. Rev. 43:425 (1991).

The preferred concentration range of the proteoglycan, hexosamine sulfate and flavone components of the oral formulations are 10-3,000 mg per tablet or capsule. The preferred concentration range for SAM is 3-1,000 mg per capsule or tablet. Generally, where present, the amounts of the unrefined kernel extract are at least three times those of the other active ingredients, preferably 300-1200 mg. The number of capsules or tablets to be taken per day is determined by the nature and severity of the medical condition, and is readily determinable by the patient's health provider. Other representative formulations are described in the examples below.

The compositions of the invention may be formulated in any standard means of introducing pharmaceuticals into a patient, e.g., by means of tablets or capsules. The compositions of the invention include ointments and creams for skin conditions, mouth washes and toothpaste for periodontal diseases, and solutions for nasal aerosols. Standard excipients and carriers for the active ingredients of the inventive compositions are described in Remington's Pharmaceutical Sciences, Mack Publishing Co., Easton, Pa.

Although not bound by any particular mechanism of action of the components of the claimed compositions, the inventor contemplates that the proteoglycan inhibits the activation and degranulation of the relevant mast cells, while the flavone inhibits the secretion of inflammatory biomolecules from these mast cells. "Activation" and "degranulation" of mast cells are defined herein as is standard and well known in this art, that is, to mean synthesis and secretion from the activated mast cell of any type of molecule(s) that alone or in combination triggers inflammatory processes.

EXAMPLES

Example 1

Table 1 compares chondroitin sulfate-containing commercial products to the present compositions.

TABLE I

Comparison of Chondroitin Sulfate-Containing Products to Present Invention

| Product | Most Available Compositions | Present Invention |
| --- | --- | --- |
| Main ingredient | Mixture of chondroitins | Non-bovine chondroitin sulfate, preferably the C type |
| Source | Cow trachea | Shark cartilage |
| Amount per capsule or tablet | 100-300 | 10-3000 mg |
| Degree of sulfation | Low, if any | High |
| Absorption from g.i. tract | <5% | >15% |

TABLE I-continued

Comparison of Chondroitin Sulfate-Containing Products to Present Invention

| Product | Most Available Compositions | Present Invention |
|---|---|---|
| Target | Unknown | Mast cells, inflammatory cells |
| Other ingredients | Vitamins, fish oils (some preparations) | Flavones, unrefined kernel olive oil, SAM, histamine-1 receptor antagonists, histamine-3 receptor agonists, CRH antagonists, polyamines, caffeine, folic acid |
| Advantages | None known | Anti-allergic, anti-inflammatory, anti-oxidant, cytoprotective |
| Adverse effects | Risk of mad cow disease, spongiform encephalopathy, stomach upset, allergy to fish products | None known |
| Relevant conditions | Osteoarthritis | Allergic inflammation angina, asthma coronary artery disease, arthritis (osteoarthritis or rheumatoid arthritis), chronic prostatitis, eczema, fibromyalgia, interstitial cystitis, irritable bowel syndrome, inflammatory bowel disease, migraines, multiple sclerosis, psoriasis, periodontal disease, flush syndrome, cancer (including hormonally-dependent forms). |
| Scientific publications | None found | Theoharides et al. Br J Pharm 131:1039 (2000) Middleton et al. Pharm Rev 52:673 (2000) |

In all examples, chondroitin sulfate is to assumed to be of a non-bovine variety.

Example 2

Composition For Protecting Against Inflammatory Diseases
Two capsules to be taken orally 2-3 times daily, at least one hour before meals

| Ingredients, per capsule. | mg: |
|---|---|
| Chondroitin sulfate | 150-300 |
| D-Glucosamine sulfate | 150-300 |
| Quercetin | 150-300 |
| Olive kernel extract | 350-1200 |

Example 3

Composition For Protecting Against Arthritis

| Ingredients per capsule. | mg: |
|---|---|
| D-Glucosamine sulfate | 150-300 |
| Chondroitin sulfate | 150-300 |
| Sodium hyaluronate | 100-200 |
| Quercetin | 150-300 |
| Olive kernel extract | 350-1200 |

Example 4

Topical Composition For Protecting Against Arthritis
Skin ointment or cream. Apply three times per day to affected areas.

| Ingredients | % by weight |
|---|---|
| D-glucosamine sulfate | 5 |
| Condroitin sulfate | 5 |
| Sodium hyaluronate | 0.5 |
| Bitter willow bark extract | 5 |
| Quercetin | 3 |
| Aloe vera | 10 |
| Olive kernel extract | 5 |

Example 5

Composition For Protecting Against Cardiovascular Disease

| | mg/capsule: |
|---|---|
| Chondroitin sulfate | 50 |
| Kaempferol | 100 |
| S-adenosylmethionine | 50 |
| Niacin | 0.01 |
| Olive kernel extract | 350-1200 |
| Bitter willow bark extract | 5% by weight |
| Polyunsaturated fatty acids (DHA, DPA) | 100-600 |

Example 6

Composition For Protecting Against Periodontal Disease

Mouthwash:

| | |
|---|---|
| Chondroitin sulfate | 0.4 M |
| Quercetin | 0.4 M |
| In a standard mouthwash vehicle | |

Example 7

Toothpaste Composition

| Toothpaste, | mg %: |
|---|---|
| Chondroitin sulfate | 5 |
| Quercetin | 3 |
| D-glucosamine sulfate | 5 |
| Olive kernel extract | 1 |
| In a standard toothpaste vehicle | |

Example 8

Sunscreen composition

| Ingredients | % by weight |
|---|---|
| Chondroitin sulfate | 5 |
| D-glucosamine sulfate | 5 |
| Quercetin | 3 |
| Aloe vera | 10 |
| Olive kernel extract | 5 |
| Sun screen (e.g., $TiO_2$) | 5 |

Example 9

Composition For Protecting Against Migraine Headaches

| Ingredients, | mg: |
|---|---|
| Chondroitin sulfate | 50 |
| Quercetin | 100 |
| Azatadine | 4 |
| Optionally, a CRH-receptor antagonist | 5-300 |

Example 10

Oral Composition For Protecting Against Inflammatory Processes in Relapsing Multiple Sclerosis

| Ingredients, | mg/day |
|---|---|
| Chondroitin sulfate | 50-300 |
| Quercetin or myricetin | 50-300 |
| Hydroxyzine | 50-300 |
| Optionally, olive kernel extract | 350-1200 |
| Optionally, interferon-beta | 8 million IU Betaferon (Schering), s.c., on alternate days or 30 µg (Avonex, Biogen) i.m. once weekly |
| Optionally, a CRH receptor antagonist | 5 |

Example 11

Composition For Protecting Against Cystitis And Prostatitis

| Ingredients, | mg/capsule or tablet: |
|---|---|
| *D-glucosamine sulfate | 50 |
| *Chondroitin sulfate | 100-300 |
| *Sodium hyaluronate | 200 |
| *Quercetin | 100-400 |
| *Olive kernel extract | 350-1200 |

Example 12

Composition For Protecting Against "Flush"

| Ingredients, | per capsule: |
|---|---|
| *Chondroitin sulfate | 50 mg |
| *Quercetin | 150-350 mg |
| *Optionally, olive kernel extract | 100-750 mg |
| *Bitter willow bark extract | 5% by weight |
| *Optionally, cyproheptadine or azatadine | 4 mg |

Example 13

Cream Composition For Protecting Against Skin Allergy

| Ingredients: | % by weight |
|---|---|
| *Aloe vera | 5 |
| *Non bovine chondroitin sulfate | 5 |
| *Myricetin | 5 |
| *Alpha-tocopherol | 5 |
| *Olive kernel extract | 5 |
| *Aloe vera | 10 |
| *Optionally, azelastine or hydroxyzine | 5 |

Example 14

Composition For Protecting Against Allergies and Allergic Asthma

| Ingredients, | mg/tablet |
|---|---|
| *Myricetin | 500 |
| *Chondroitin sulfate | 200 |
| *Optionally, azelastine | 4 |
| *Rutin | 500 |
| *Optionally, hydroxyzine | 25 |

Example 15

Composition For Protecting Against Hormonally-Dependent Cancers

| Ingredients, | mg/day |
|---|---|
| Chondroitin sulfate | 50-300 |
| Quercetin | 25-250 |
| Genestein | 50-300 |
| Phenoxodiol isoflavone | 500-1000 |
| Olive kernel extract | 350-1200 |
| Optionally, tomoxifen or raloxifen | About 10 |

Example 16

| Composition For Protecting Against Allergic Conjunctivitis | |
|---|---|
| Ingredients: | |
| *Quercetin | 0.05% |
| *Chondroitin sulfate | 2.0% |
| *Optionally azelastine | 0.05% |

Example 17

Effect of Olive Kernel Extract on Absorption of a Proteoglycan Sulfate In Vivo

Chondroitin sulfate was tritiated by New England Nuclear Corp. to a specific activity of 4.3 mCi/ml.
Unlabeled chondroitin sulfate was dissolved in olive kernel extract at a ratio of about 55 w/v chondroitin sulfate powder to about 450 w/v of olive kernel extract (2.9% acidity as oleic acid, 1.03% water, 0.08% hexane). To this solution was added 20.2 microcuries of the labeled chondroitin sulfate. AAA gelatin capsules were filled with the resulting solution using an aluminum template molding device.

The laboratory animals (250 g male Sprague-Dawley rats) were kept overnight without food but with free access to water. One capsule containing the above-described chondroitin sulfate-olive kernel extract solution was given to each rat per os. Control animals were given the equivalent amount of chondroitin, but without olive kernel extract. The animals were then given free access to food. Serum radioactivity was measured 8 hours thereafter in a beta scintillation counter.

The results showed that, in control animals, about 3.9%+/−0.4% (n=3) of the dose of labeled chondroitin sulfate reached the circulation. In sharp contrast, in animals given the olive kernel extract along with the labeled chondroitin sulfate, about 14.3%+/−0.7% (n=4) of the dose was absorbed into the general circulation.

These results demonstrate that olive kernel extract increased by almost 400% the absorption of a proteoglycan from the intestine into the general circulation.

Parallel experiments with codfish oil, corn oil and olive oil (from the flesh of the olive) were comtemplated, but chondroitin sulfate solubility in these oils was insufficient to meet the requirements of the experiment.

Example 18

| Composition for Protecting Against Endometriosis | |
|---|---|
| Ingredients | mg/tablet |
| *Rutin | 500 |
| *Chondroitin sulfate | 500 |

I claim:

1. A composition for treating inflammatory components of a hormonally-dependent cancer, comprising, in therapeutically effective amounts, a sulfated proteoglycan, one or more flavonoid compounds, one or more isoflavonoid compounds, and olive kernel extract, wherein the ratio of the sulfated proteoglycan to the flavonoid ranges from 1:5 to 12:1, the ratio of the sulfated proteoglycan to the isoflavonoid ranges from 1:20 to 6:1, and the ratio of the sulfated proteoglycan to the olive kernel extract ranges from 1:24 to 6:7, and wherein the olive kernel extract is unrefined and has oleic acid-related acidity <3% and water content <1%.

2. The composition of claim 1, further comprising a chemotherapeutic agent.

3. The composition of claim 2, wherein said proteoglycan is chondroitin sulfate, said flavonoid compound is quercetin, said isoflavonoid compound is phenoxodiol or genistein, and said chemotherapeutic agent is tamoxifen or raloxifen.

4. The composition of claim 1, comprising, in mg, chondroitin sulfate, 50-300; olive kernel extract, 350-1200; quercetin, 25-250; phenoxodiol isoflavone, 500-1000; and genistein, 50-300.

5. The composition of claim 3, wherein said tamoxifen or raloxifen is in the amount of 10 mg.

6. The composition of claim 1, wherein said cancer is selected from the group consisting of breast cancer, ovarian cancer, pancreatic cancer, testicular cancer, prostate cancer, pituitary cancer, endometrial cancer, and melanoma.

7. The composition of claim 1, comprising therapeutically effective amounts of chondroitin sulfate, olive kernel extract, phenoxodiol isoflavone, quercetin, and genistein.

8. The composition of claim 7, wherein the chondroitin sulfate is non-bovine chondroitin sulfate.

9. The composition of claim 8, further comprising a therapeutically effective amount of tamoxifen or raloxifen.

10. A method of treating the inflammatory components of a hormonally-dependent cancer, comprising the oral administration of a composition of claim 1.

11. A method of treating both the inflammatory components and the growth components of a hormonally-dependent cancer, comprising the administration of the composition of claim 3.

12. A method of treating the inflammatory components of a hormonally-dependent cancer, comprising the oral administration of a composition of claim 4.

13. A method of treating both the inflammatory components and the growth components of a hormonally-dependent cancer, comprising the administration of the composition of claim 5.

14. A composition for treating a hormonally-dependent cancer, comprising, in therapeutically effective amounts, a sulfated proteoglycan, one or more flavonoid compounds, one or more isoflavonoid compounds, olive kernel extract, and a chemotherapeutic agent, wherein the ratio of the sulfated proteoglycan to the flavonoid ranges from 1:5 to 12:1, the ratio of the sulfated proteoglycan to the isoflavonoid ranges from 1:20 to 6:1, the ratio of the sulfated proteoglycan to the olive kernel extract ranges from 1:24 to 6:7, and the ratio of the sulfated proteoglycan to the chemotherapeutic agent ranges from 5:1 to 30:1, and wherein the olive kernel extract is unrefined and has oleic acid-related acidity <3% and water content <1%.

15. The composition of claim 14, wherein said proteoglycan is chondroitin sulfate, said flavonoid compound is quercetin, said isoflavonoid compound is phenoxodiol, and said chemotherapeutic agent is tamoxifen or raloxifen.

16. The composition of claim 14, comprising, in mg, non-bovine chondroitin sulfate, 50-300; olive kernel extract, 350-1200; quercetin, 25-250; phenoxodiol isoflavone, 500-1000; genistein, 50-300; and tamoxifen, 10.

17. The composition of claim 14, wherein said cancer is selected from the group consisting of breast cancer, ovarian cancer, pancreatic cancer, testicular cancer, prostate cancer, pituitary cancer, endometrial cancer, and melanoma.

18. The composition of claim 14, comprising therapeutically effective amounts of chondroitin sulfate, olive kernel extract, phenoxodiol isoflavone, quercetin, and genistein.

19. The composition of claim 18, wherein the chondroitin sulfate is non-bovine chondroitin sulfate.

20. The composition of claim 19, wherein the chemotherapeutic agent is a therapeutically effective amount of tamoxifen or raloxifen.

21. The composition of claim 14, comprising, in mg, non-bovine chondroitin sulfate, 50-300; olive kernel extract, 350-1200; quercetin, 25-250; phenoxodiol isoflavone, 500-1000; and genistein, 50-300; and raloxifen, 10.

* * * * *